(12) United States Patent
Sakakura et al.

(10) Patent No.: US 10,118,148 B2
(45) Date of Patent: Nov. 6, 2018

(54) REACTOR

(71) Applicant: IHI CORPORATION, Tokyo (JP)

(72) Inventors: Shigeki Sakakura, Tokyo (JP);
Nobuyuki Honma, Tokyo (JP);
Takashi Nishii, Tokyo (JP); Tomohiro Kaneko, Tokyo (JP); Rie Harada, Tokyo (JP); Kunitaka Masaki, Tokyo (JP); Hiroyuki Kamata, Tokyo (JP);
Koki Hamada, Tokyo (JP); Akihisa Yano, Tokyo (JP); Tatsuya Oka, Tokyo (JP); Yusuke Takeuchi, Tokyo (JP)

(73) Assignee: IHI CORPORATION, Tokyo (JP)

( * ) Notice: Subject to any disclaimer, the term of this patent is extended or adjusted under 35 U.S.C. 154(b) by 0 days.

(21) Appl. No.: 15/820,548

(22) Filed: Nov. 22, 2017

(65) Prior Publication Data
US 2018/0093241 A1 Apr. 5, 2018

Related U.S. Application Data

(63) Continuation of application No. PCT/JP2016/066992, filed on Jun. 8, 2016.

(30) Foreign Application Priority Data

Jun. 8, 2015 (JP) .................. 2015-115659

(51) Int. Cl.
*B01J 19/00* (2006.01)
*B01J 19/24* (2006.01)
(Continued)

(52) U.S. Cl.
CPC ............ *B01J 12/007* (2013.01); *B01J 19/24* (2013.01); *B01J 19/245* (2013.01); *B01J 19/249* (2013.01);
(Continued)

(58) Field of Classification Search
CPC . B01J 12/00; B01J 12/007; B01J 19/00; B01J 19/24; B01J 19/2445; B01J 19/245;
(Continued)

(56) References Cited

U.S. PATENT DOCUMENTS 7,754,935 B2 * 7/2010 Brophy ................. B01F 5/0475
422/132
9,776,164 B2 * 10/2017 Kamata ................ B01F 5/0082
(Continued)

FOREIGN PATENT DOCUMENTS

JP S58-010583 U1 1/1983
JP H06-111838 A 4/1994
(Continued)

OTHER PUBLICATIONS

International Search Report received for PCT Patent Application No. PCT/JP2016/066992 dated Aug. 30, 2016, 4 pages (2 pages of English translation of International Search Report, and 2 pages of International Search Report).
(Continued)

*Primary Examiner* — Natasha E Young

(57) ABSTRACT

An end surface of each first side wall, an end surface of each first middle wall, and an end surface of each first end wall are joined to an adjacent second structure by diffusion bonding, an end surface of each second side wall, an end surface of each second middle wall, and an end surface of each second end wall are joined to an adjacent first structure or a lid structure by diffusion bonding, a thickness of each first side wall is greater than or equal to a thickness of each first middle wall, and a thickness of each second side wall is greater than or equal to a thickness of each second middle wall.

18 Claims, 8 Drawing Sheets

(51) Int. Cl.
  *C01B 3/38* (2006.01)
  *C07C 1/00* (2006.01)
  *F28D 9/00* (2006.01)
  *F28F 3/08* (2006.01)
  *B01J 12/00* (2006.01)
  *F28F 3/00* (2006.01)
  *C01B 3/48* (2006.01)
  *C07C 1/04* (2006.01)

(52) U.S. Cl.
  CPC ............ *B01J 19/2445* (2013.01); *C01B 3/38* (2013.01); *C01B 3/384* (2013.01); *C01B 3/48* (2013.01); *C07C 1/041* (2013.01); *F28D 9/00* (2013.01); *F28D 9/0093* (2013.01); *F28F 3/00* (2013.01); *F28F 3/08* (2013.01); *B01J 2219/2465* (2013.01); *C01B 2203/0233* (2013.01); *C01B 2203/0238* (2013.01); *C01B 2203/0283* (2013.01); *C01B 2203/0833* (2013.01); *C01B 2203/0883* (2013.01); *C01B 2203/1241* (2013.01)

(58) Field of Classification Search
  CPC .... B01J 19/248; B01J 19/249; B01J 2219/24; B01J 2219/2401; B01J 2219/245; B01J 2219/2461; B01J 2219/2465; C01B 3/00; C01B 3/02; C01B 3/32; C01B 3/34; C01B 3/38; C01B 3/384; C01B 3/48; C01B 2203/00–2203/0205; C01B 2203/0227; C01B 2203/0233; C01B 2203/0238; C01B 2203/0283; C01B 2203/08; C01B 2203/0805; C01B 2203/0833; C01B 2203/0872; C01B 2203/0883; C01B 2203/12–2203/1211; C01B 2203/1235; C01B 2203/1241; C07C 1/00–1/041; F28D 9/00; F28D 9/0093; F28F 3/00; F28F 3/08
  See application file for complete search history.

(56) References Cited

U.S. PATENT DOCUMENTS

| | | |
|---|---|---|
| 2003/0152488 A1 | 8/2003 | Tonkovich et al. |
| 2004/0228781 A1 | 11/2004 | Tonkovich et al. |
| 2004/0229752 A1 | 11/2004 | Long et al. |
| 2006/0151160 A1 | 7/2006 | Take |
| 2007/0140955 A1 | 6/2007 | Tonkovich et al. |
| 2008/0050634 A1 | 2/2008 | Park et al. |
| 2008/0226517 A1 | 9/2008 | Vitucci |
| 2010/0160705 A1 | 6/2010 | Kösters |
| 2011/0002818 A1 | 1/2011 | Tonkovich et al. |
| 2012/0031349 A1 | 2/2012 | Tonkovich et al. |
| 2012/0171517 A1 | 7/2012 | Yuschak et al. |
| 2012/0210995 A1 | 8/2012 | West |
| 2014/0030789 A1* | 1/2014 | Katz ............... C12N 9/10 435/188 |
| 2015/0064078 A1 | 3/2015 | Kösters |
| 2016/0144336 A1 | 5/2016 | Hamada et al. |
| 2018/0113494 A1* | 4/2018 | Kikuchi .............. G06F 1/20 |
| 2018/0179048 A1* | 6/2018 | Schenk ............ B81C 1/00158 |

FOREIGN PATENT DOCUMENTS

| | | | |
|---|---|---|---|
| JP | H06-345405 A | 12/1994 | |
| JP | 2003-183003 A | 7/2003 | |
| JP | 2006-336873 A | 12/2006 | |
| JP | 2007-534457 A | 11/2007 | |
| JP | 2008-518184 A | 5/2008 | |
| JP | 2008-526501 A | 7/2008 | |
| JP | 4378526 B2 | 10/2009 | |
| JP | 2010-012466 A | 1/2010 | |
| JP | 2010-532707 A | 10/2010 | |
| JP | 4963372 B2 | 4/2012 | |
| JP | 2013-508150 A | 3/2013 | |
| JP | 2013-521465 A | 6/2013 | |
| JP | 2014-084334 A | 5/2014 | |
| WO | WO-2014208646 A1 * | 12/2014 | ............ B01F 5/0082 |
| WO | 2015/037597 A1 | 3/2015 | |

OTHER PUBLICATIONS

Taiwan Patent Office, Office Action and Search Report, issued in TW Patent Application No. 105118227, which is a Taiwanese counterpart of JP Appl. Ser. No. 2015-115659, dated Jun. 26, 2017, 6 pages (5 pages of Office Action and 1 page of Search Report).

* cited by examiner

REACTOR

CROSS REFERENCE TO RELATED APPLICATIONS

This application is a continuation application of International Application No. PCT/JP2016/066992, now WO 2016/199790, filed on Jun. 8, 2016, which claims priority to Japanese Patent Application No. 2015-115659, filed on Jun. 8, 2015, the entire contents of which are incorporated by reference herein.

BACKGROUND

1. Technical Field

Embodiments described herein relate to a reactor for causing a reaction of a first fluid (such as a reaction fluid) by a heat exchange between the first fluid and a second fluid (such as a heat medium) to generate a product (a reaction product).

2. Description of the Related Art

Japanese Unexamined Patent Application Publication No. H06-345405 (Patent Literature 1), Japanese Unexamined Patent Application Publication No. 2003-183003 (Patent Literature 2) and Japanese Translation of PCT International Application Publication No. 2010-532707 (Patent Literature 3) disclose a multi-tubular reactor including multiple reactor tubes having reaction channels therein through which a raw material fluid flows, and a burner for heating the multiple reactor tubes. Japanese Translation of PCT International Application Publication No. 2008-526501 (Patent Literature 4) discloses a multilayer reactor including a reactor module in which a plurality of flow channels serving as a reaction space for a raw material fluid and a plurality of flow channels for heating the raw material fluid are alternately stacked in the vertical direction. International Publication WO 2015/037597 (Patent Literature 5), Japanese Translation of PCT International Application Publication No. 2013-508150 (Patent Literature 6) and Japanese Unexamined Patent Application Publication No. 2014-084334 (Patent Literature 7) disclose a reactor including flow channels.

SUMMARY

In a multi-tubular reactor, multiple reactor tubes are preferred to be arranged in an appropriate state (set to an appropriate arrangement state) in order to prevent uneven reaction (avoid ununiformity) in reaction channels while applying heat substantially equally to the respective reaction channels. When the capacity of the reactor is changed, the reactor should be redesigned entirely, which would spend a great deal of load and time.

A multilayer reactor can apply heat substantially equally to first flow channels (flow channels for reaction) regardless of the number of first structures (such as structures for reaction) and second structures (such as structures for supplying a heat medium) to be stacked. However, a reactor core is preferred to be housed in a container (pressure vessel) resistant to a pressure difference between the inside and the outside because the reactor core itself does not have sufficient structural strength (strength to resist pressure). Thus, when the capacity of the reactor is changed, not only the number of the first structures stacked should be changed, but also the container as a component of the reactor is preferred to be redesigned entirely, which impedes flexibility in changing the capacity.

It should be noted that the problems described above are applied to any case regardless of whether a reaction of a first fluid is an endothermic reaction caused by heating the first fluid or an exothermic reaction caused by cooling the first fluid.

One object of the present disclosure is to provide a reactor having flexibility in changing a capacity without great change in design of the entire reactor.

A reactor according to an aspect of the present disclosure causes a reaction of a first fluid by a heat exchange between the first fluid and a second fluid to generate a product, the reactor including: a plurality of first structures each including: first side walls provided on both sides in a first direction on one surface of a first base plate and extending in a second direction perpendicular to the first direction; a plurality of first middle walls arranged at intervals in the first direction between the paired first side walls on the one surface of the first base plate and extending in the second direction; and first flow channels provided between each first side wall and the adjacent first middle wall and between the respective first middle walls adjacent to each other so that the first fluid flows therethrough; a plurality of second structures coexisting with and stacked on the plural first structures in a third direction perpendicular to the first direction and the second direction, the second structures each including: second side walls provided on both sides in the first direction on one surface of a second base plate and extending in the second direction; a plurality of second middle walls arranged at intervals in the first direction between the paired second side walls on the one surface of the second base plate and extending in the second direction; and second flow channels provided between each second side wall and the adjacent second middle wall and between the respective second middle walls adjacent to each other so that the second fluid flows therethrough; and a lid structure provided on the second structure located on one end side in the third direction to cover the plural second flow channels, wherein end surfaces of the first side walls and end surfaces of the first middle walls are joined to the adjacent second structure, end surfaces of the second side walls and end surfaces of the second middle walls are joined to the adjacent first structure or the lid structure, a thickness of the first side walls is greater than or equal to a thickness of the first middle walls, and a thickness of the second side walls is greater than or equal to a thickness of the second middle walls.

The reactor may be applicable to a case in which both the first fluid and the second fluid cause an endothermic reaction or an exothermic reaction, or a case in which one of the first fluid and the second fluid causes either of the reactions and the other fluid allows a flow of a heat medium. As used herein, the expression "coexisting with and stacked on" includes a case in which the plural first structures and the plural second structures are alternately stacked and a case in which at least a pair of either the first structures or the second structures laid on top of each other is stacked on the other one of the first structures and the second structures.

According to the present disclosure, the reactor can apply heat substantially equally to the respective first flow channels regardless of the number of the first structures and the like to be stacked, and ensure sufficient strength of a reactor core to resist pressure without the reactor core housed in a container. Accordingly, the reactor increases flexibility in changing the capacity such that the number of the first structures and the like to be stacked is merely changed without great change in design of the reactor.

DESCRIPTION OF THE EMBODIMENTS

Some embodiments of the present disclosure will be described with reference to the drawings. An embodiment is illustrated below with a case in which a first fluid is a raw material fluid and a second fluid is a heat medium.

Figure 1:
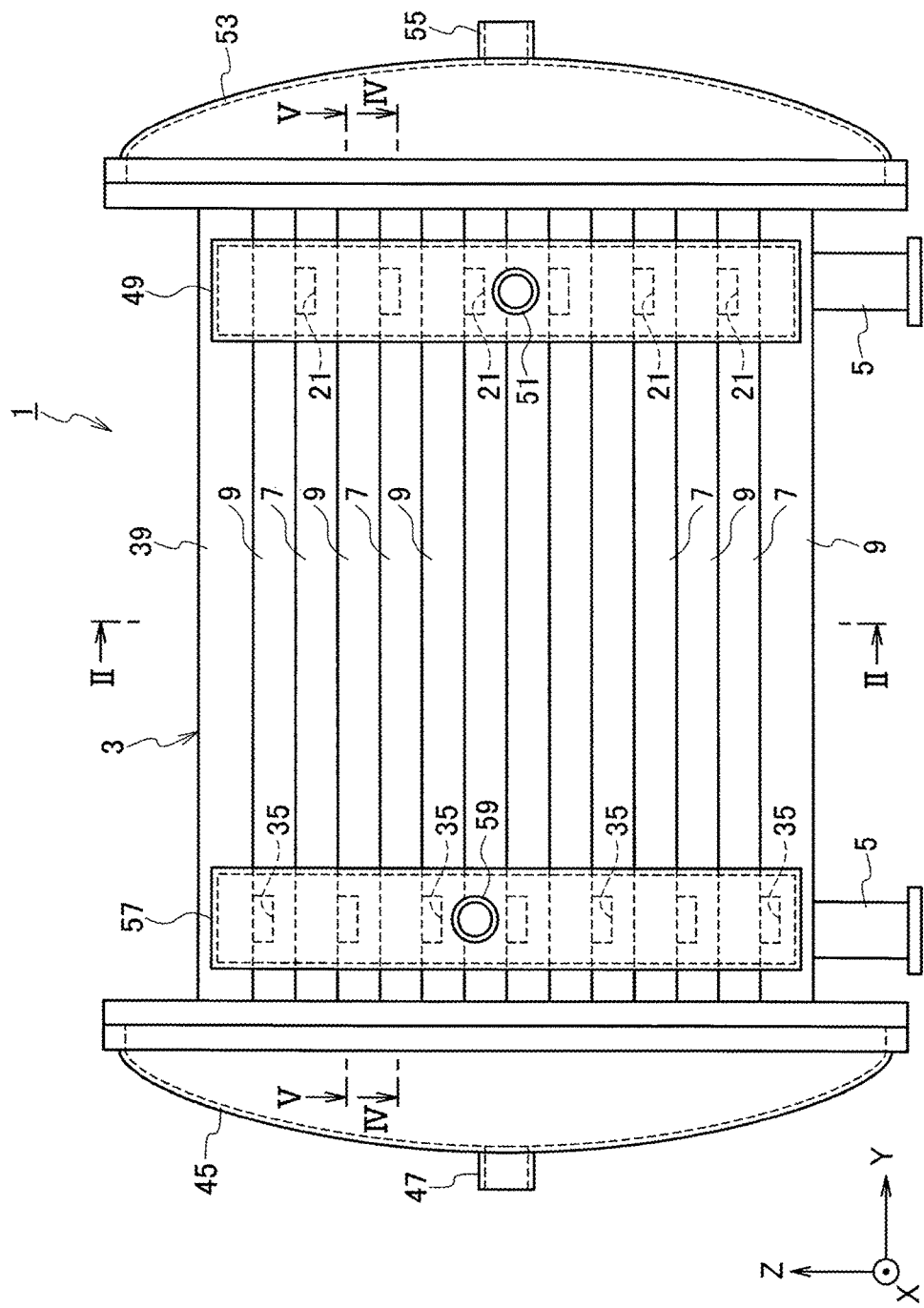
FIG. 1 is a schematic front view of a reactor according to one embodiment of the present disclosure.
Figure 4:
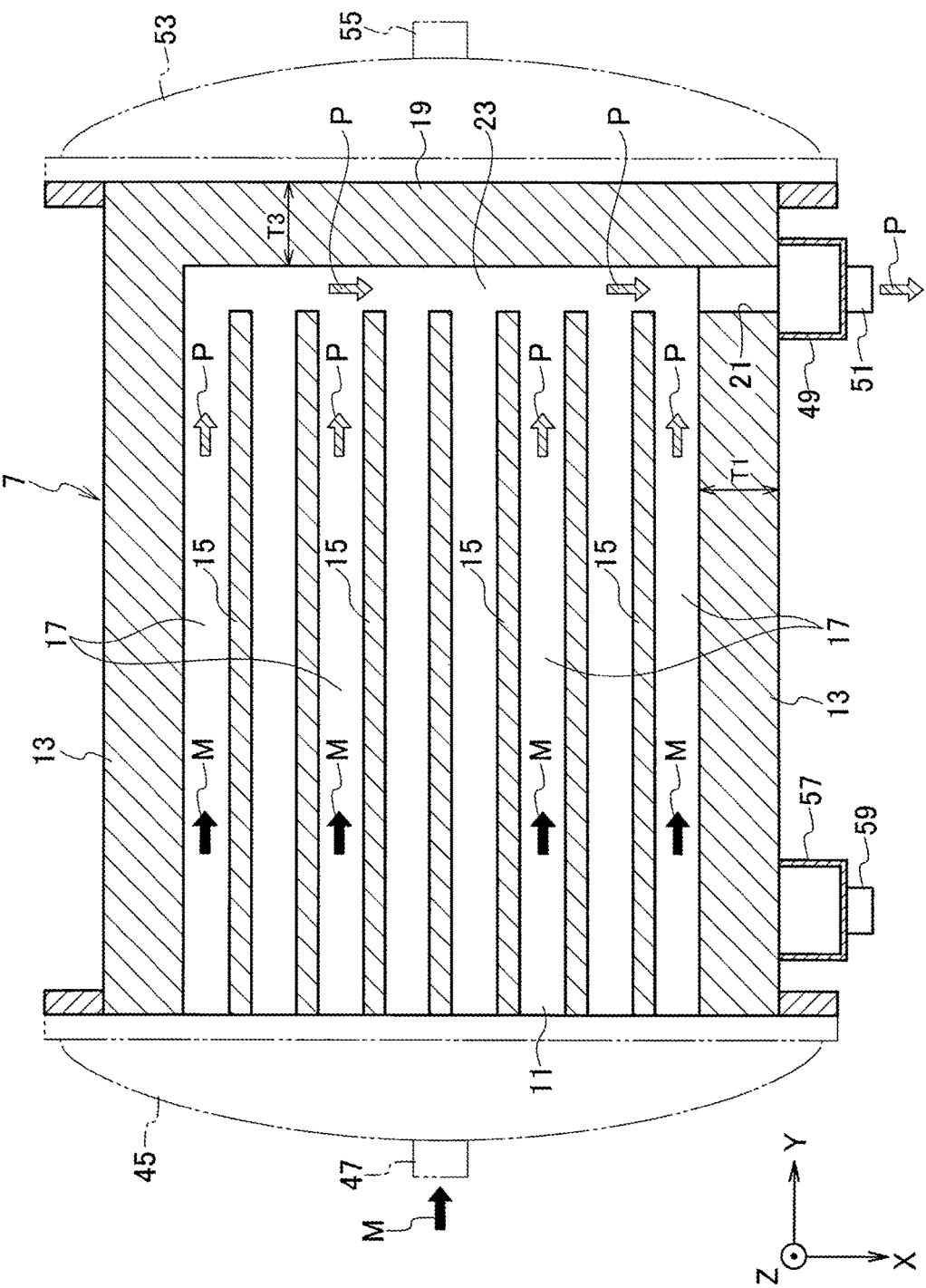
FIG. 4 is a cross-sectional view taken along line IV-IV of FIG. 1.

As shown in FIG. 1, a reactor (a multilayer reactor) 1 according to the present embodiment heats or cools a first fluid M by a heat exchange between the first fluid M (see FIG. 4) and a second fluid HC (see FIG. 5) to cause a reaction of the first fluid M, so as to produce a product P (see FIG. 4). Before a specific configuration of the reactor 1 is described, the reaction of the first fluid M is briefly described below.

The reaction of the first fluid M includes two types: an endothermic reaction caused by heating the first fluid M and an exothermic reaction caused by cooling the first fluid M. Examples of the former reaction (the endothermic reaction) include a steam reforming reaction of methane as represented by the following chemical equation (1), and a dry reforming reaction of methane as represented by the following chemical equation (2).

$$CH_4+H_2O \rightarrow 3H_2+CO \quad (1)$$

$$CH_4+CO_2 \rightarrow 2H_2+2CO \quad (2)$$

Examples of the latter reaction (the exothermic reaction) include a shift reaction as represented by the following chemical equation (3), a methanation reaction as represented by the following chemical equation (4), and a Fischer tropsch synthesis reaction as represented by the following chemical equation (5).

$$CO+H_2O \rightarrow CO_2+H_2 \quad (3)$$

$$CO+3H_2 \rightarrow CH_4+H_2O \quad (4)$$

$$(2n+1)H_2+nCO \rightarrow C_nH_{2n+2}+nH_2O \quad (5)$$

The reaction of the first fluid M is not limited to the steam reforming reaction of methane and the like, and other examples thereof include an acetylation reaction, an addition reaction, an alkylation reaction, a dealkylation reaction, a hydrodealkylation reaction, a reductive alkylation reaction, an amination reaction, an aromatization reaction, an acylation reaction, a self-heating reforming reaction, a carbo-nylation reaction, a decarbonylation reaction, a reductive carbonylation reaction, a carboxylation reaction, a reductive carboxylation reaction, a reductive coupling reaction, a condensation reaction, a cracking reaction, a hydrocracking reaction, a cyclization reaction, a cyclo-oligomerization reaction, a dehalogenation reaction, a dimerization reaction, an epoxidation reaction, an esterification reaction, an exchange reaction, a halogenation reaction, a hydrohalogenation reaction, a homologation reaction, a hydration reaction, a dehydration reaction, a hydrogenation reaction, a dehydrogenation reaction, a hydrocarboxylation reaction, a hydroformylation reaction, a hydrogenolysis reaction, a hydrometalation reaction, a hydrosilylation reaction, a hydrolyzation reaction, a hydroprocessing reaction, an isomerization reaction, a methylation reaction, a demethylation reaction, a substitution reaction, a nitration reaction, an oxidation reaction, a partial oxidation reaction, a polymerization reaction, a reduction reaction, a reverse water-gas shift reaction, a sulfonation reaction, a telomerization reaction, a transesterification reaction, and a trimerization reaction.

The second fluid HC used may be high-temperature gas such as fuel gas, water, and a refrigerant, and selected as appropriate depending on the reaction type and conditions of the first fluid M. For example, when the reaction of the first fluid M is a steam reforming reaction of methane, the second fluid HC used is high-temperature gas such as fuel gas. When the reaction of the first fluid M is a dry reforming reaction of methane, the second fluid HC used is high-temperature gas or the like. When the reaction of the first fluid M is a shift reaction, the second fluid HC used is oil, water (including steam), molten salt, or the like. When the reaction of the first fluid M is a methanation reaction, the second fluid HC used is oil, water (including steam), molten salt, or the like. When the reaction of the first fluid M is a Fischer tropsch synthesis reaction, the second fluid HC used is water (including steam) or the like.

Figure 2:
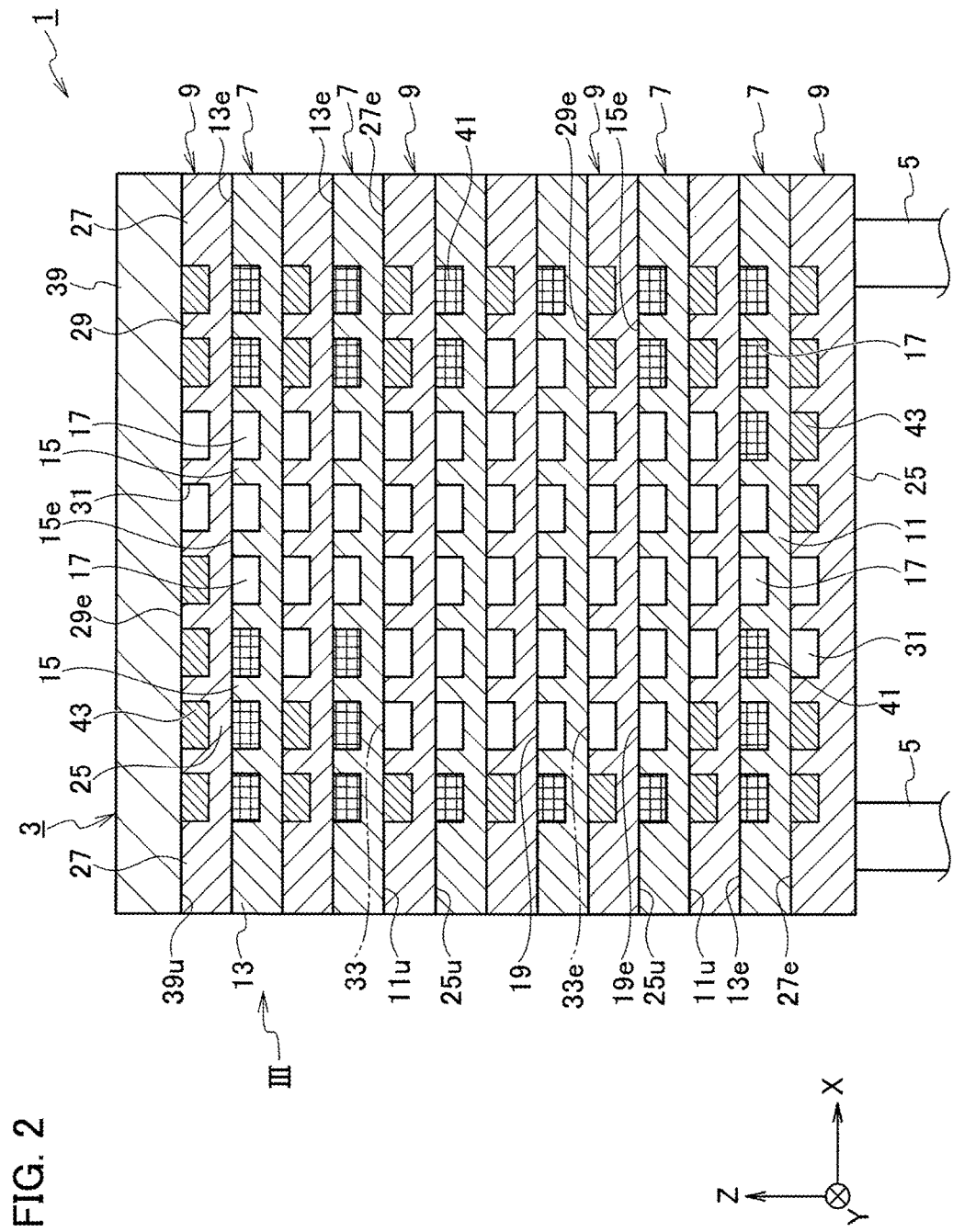
FIG. 2 is an enlarged cross-sectional view taken along line II-II of FIG. 1.
Figure 6:
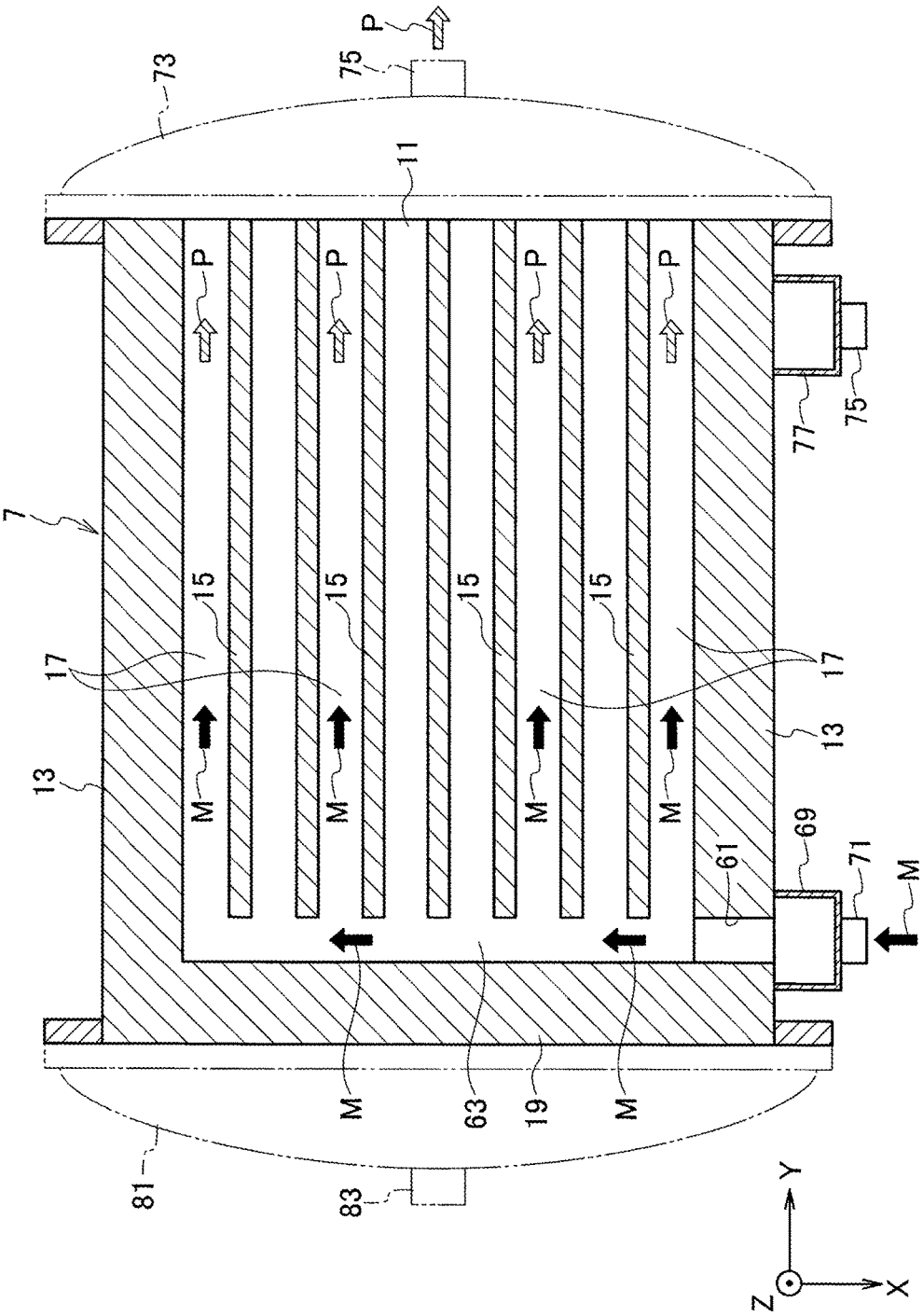
FIG. 6 is a cross-sectional view for illustrating modified example 1 of one embodiment.
Figure 8A:
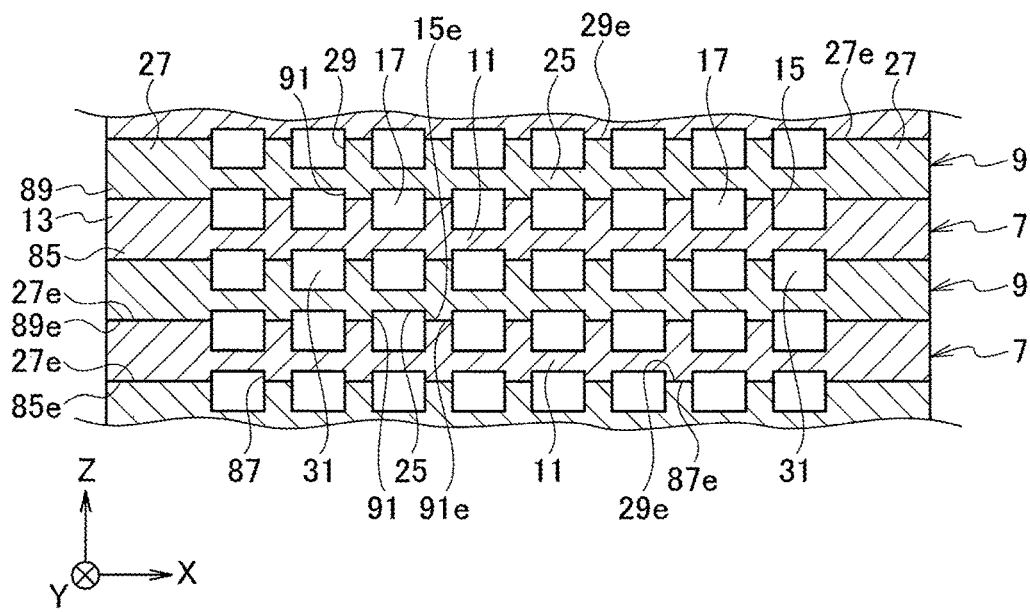
FIG. 8A is a cross-sectional view for illustrating modified example 2 of one embodiment.
Figure 8B:
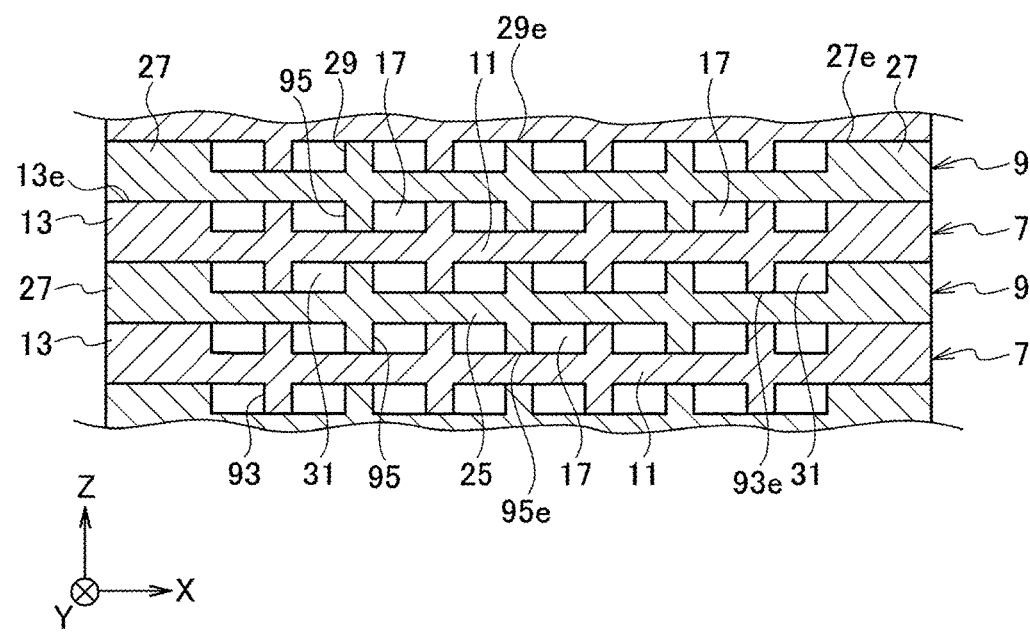
FIG. 8B is a cross-sectional view for illustrating modified example 2 of one embodiment.

The specific configuration of the reactor 1 is described below. It should be noted that a front-rear direction which is a depth direction of the reactor 1 corresponds to a first direction (X direction) as set forth in appended claims, a lateral direction which is a width direction of the reactor 1 corresponds to a second direction (Y direction) as set forth in appended claims, and a vertical direction which is a height direction of the reactor 1 corresponds to a third direction (Z direction) as set forth in appended claims. FIG. 2 schematically illustrates only part of catalyst members and part of fins. FIG. 4 omits the illustration of the catalyst members. FIG. 6 omits the illustration of the catalyst members. FIG. 8A and FIG. 8B omit the illustration of the catalyst members and the fins.

As shown in FIG. 1 and FIG. 2, the reactor 1 includes a reactor core 3 serving as a center of the reactor 1. The reactor core 3 is installed at an appropriate position with a plurality of supporting pillars 5. The reactor core 3 includes a plurality of (multiple) rectangular first structures (reactor members) 7 for providing a reaction space for the first fluid M (for causing a reaction of the first fluid M), and a plurality of (multiple) rectangular second structures (temperature control members) 9 for heating or cooling the first fluid M. The first structures 7 and the second structures 9 are alternately stacked in the vertical direction. The arrangement of the first structures 7 and the second structures 9 is not limited to the alternately stacked state. The first structures 7 and the second structures 9 may be arranged such that at least a pair of either the first structures or the second structures laid on top of each other is stacked on the other one of the first structures and the second structures. The specific configuration of each of the first structures 7 and the second structures 9 is described below.

Figure 3:
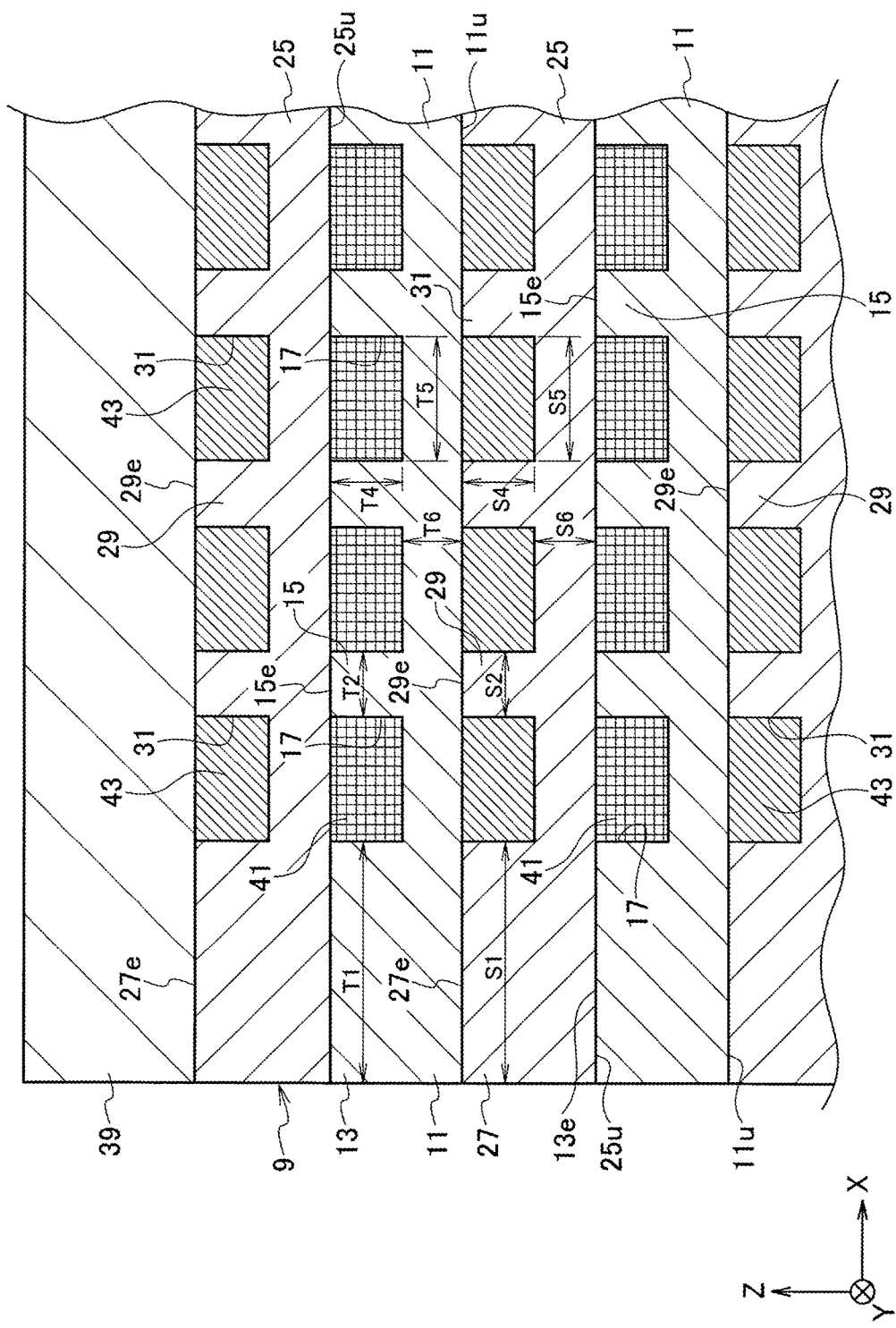
FIG. 3 is an enlarged view on arrow III of FIG. 2.

FIG. 2 to FIG. 4 illustrate the first structures 7 made of an iron alloy such as stainless steel, or a nickel alloy such as Inconel alloy 625, Inconel alloy 617, and Haynes alloy 230 (examples of heat-resistant alloys). The first structures 7 each include a first base plate 11 having a rectangular plate shape. The first base plate 11 is provided with first side walls 13 on front and rear sides on one surface (one surface in the thickness direction; the upper surface in the present embodiment). The respective first side walls 13 project upward (in one direction) and extend in the lateral direction. A plurality of first middle walls 15 are arranged at regular intervals in the front-rear direction between the pair of the first side walls 13 on one surface of the first base plate 11. The respective first middle walls 15 project upward and extend in the lateral direction. The first middle walls 15 have the same height as the first side walls 13.

A plurality of first flow channels 17 through which the first fluid M flows are provided between each first side wall 13 and the adjacent first middle wall 15 and between the respective pairs of the first middle walls 15 adjacent to each other. Namely, the plural first flow channels 17 are provided at regular intervals in the front-rear direction on one surface of the first structure 7, so that the pair of the first side walls 13 and the plural first middle walls 15 are aligned on one surface of the first base plate 11. The respective first flow channels 17 extend in the lateral direction and have a channel length (a length in the lateral direction) set at approximately 100 cm in the present embodiment, for example. The respective first flow channels 17 have a rectangular shape in cross section. The respective first flow channels 17 are open on the left side so as to introduce the first fluid M therefrom.

The first base plate 11 is provided, on the right side on one surface, with a first end wall 19 for preventing the second fluid HC from flowing into the plural first flow channels 17. The first end wall 19 projects upward and extends in the front-rear direction so as to connect the pair of the first side walls 13. The first end wall 19 has the same height as the first side walls 13 and the first middle walls 15. A first leading-out port 21 for leading the product P is provided on the right side on one of or both of the first side walls 13. A first connection flow channel 23 by which the first leading-out port 21 connects with the first flow channels 17 on the right side is provided on the right side (toward the first end wall 19) on one surface of the first base plate 11. The first connection flow channel 23 extends in the front-rear direction.

Each of the first structures 7 is manufactured such that a base material of one plate is subjected to machining processing, or may be manufactured by etching processing. Alternatively, each of the first structures 7 may be manufactured such that the pair of the first side walls 13, the plural first middle walls 15 and the first end wall 19 may be joined to the first base plate 11 by diffusion bonding. An alternative joining method may be welding or brazing. Each of the first structures 7 may be manufactured by sintering of metal powder by use of a three-dimensional printer. Each of the first structures 7 may also be manufactured by a combination of two or more methods of machining, etching, diffusion bonding, welding, brazing, and sintering of metal powder.

The reactor core 3 is schematically illustrated, and includes several tens of first structures 7 and several tens of first flow channels 17 in one first structure 7 in the present embodiment, for example. The number of each of the first end wall 19 and the first connection flow channel 23 may be changed depending on the number of the first flow channels 17. The maximum pressure in the respective first flow channels 17 when the reactor 1 is in operation is set at a predetermined level in a range of 0.0 to 20.0 MPaG which varies depending on the reaction type and conditions of the first fluid M.

Figure 5:
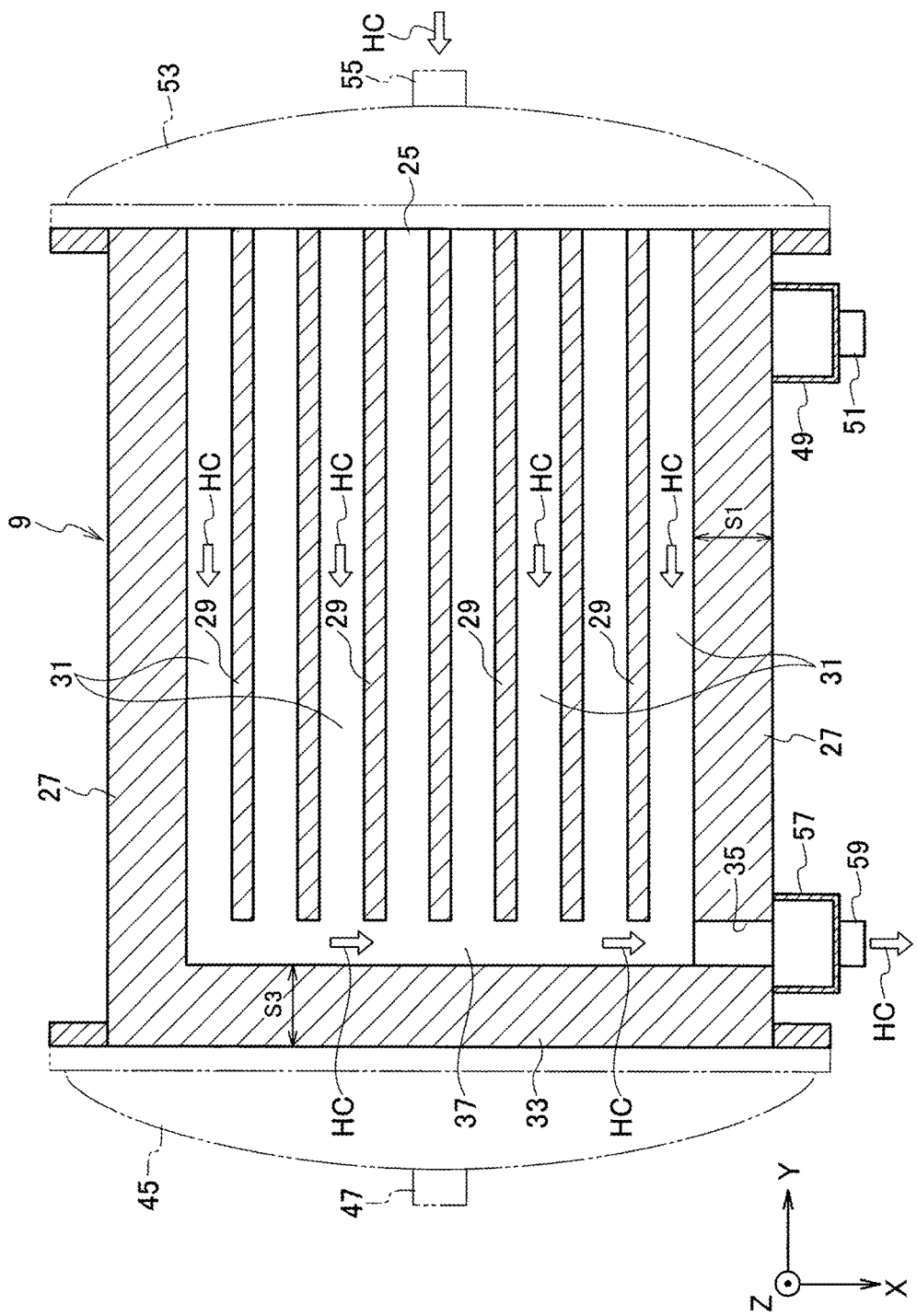
FIG. 5 is a cross-sectional view taken along line V-V of FIG. 1.

As shown in FIG. 2, FIG. 3 and FIG. 5, the second structures 9 each include a second base plate 25 having a rectangular plate shape, and are made of the same material as the first structures 7. The second base plate 25 is provided on one surface (the upper surface) with second side walls 27 on front and rear sides. The respective second side walls 27 project upward and extend in the lateral direction. A plurality of second middle walls 29 are arranged at regular intervals in the front-rear direction between the pair of the second side walls 27 on one surface of the second base plate 25. The respective second middle walls 29 project upward and extend in the lateral direction. The second middle walls 29 have the same height as the second side walls 27.

A plurality of second flow channels 31 through which the second fluid HC flows are provided between each second side wall 27 and the adjacent second middle wall 29 and between the respective pairs of the second middle walls 29 adjacent to each other. Namely, the plural second flow channels 31 are provided at regular intervals in the front-rear direction on one surface of the second structure 9, so that the pair of the second side walls 27 and the plural second middle walls 29 are aligned on one surface of the second base plate 25. The respective second flow channels 31 extend in the lateral direction and have a channel length (a length in the lateral direction) set at approximately 100 cm in the present embodiment, for example. The respective second flow channels 31 have a rectangular shape in cross section. The respective second flow channels 31 are open on the right side so as to introduce the second fluid HC therefrom. The second flow channels 31 face the corresponding first flow channels 17 in the vertical direction with the second base plate 25 or the first base plate 11 interposed therebetween.

The second base plate 25 is provided, on the left side on one surface, with a second end wall 33 for preventing the first fluid M from flowing into the plural second flow channels 31. The second end wall 33 projects upward and extends in the front-rear direction so as to connect the pair of the second side walls 27. The second end wall 33 has the same height as the second side walls 27 and the second middle walls 29. A second leading-out port 35 for leading the second fluid HC out of the second base plate 25 is provided on the left side on one of or both of the second side walls 27. A second connection flow channel 37 by which the second leading-out port 35 connects with the second flow channels 31 on the left side is provided on the left side (toward the second end wall 33) on one surface of the second base plate 25.

Each of the second structures 9 is manufactured such that a base material of one plate is subjected to machining processing, or may be manufactured by etching processing. Alternatively, each of the second structures 9 may be manufactured such that the pair of the second side walls 27, the plural second middle walls 29 and the second end wall 33 may be joined to the second base plate 25 by diffusion bonding. An alternative joining method may be welding or brazing. Each of the second structures 9 may be manufactured by sintering of metal powder by use of a three-dimensional printer. Each of the second structures 9 may also be manufactured by a combination of two or more methods of machining, etching, diffusion bonding, welding, brazing, and sintering of metal powder.

As described above, the reactor core 3 is schematically illustrated, and may include several tens of second structures 9 and several tens of second flow channels 31 in one second structure 9 in the present embodiment. The number of each of the second end wall 33 and the second connection flow channel 37 may be changed depending on the number of the second flow channels 31. The maximum pressure in the respective second flow channels 31 when the reactor 1 is in operation is set at a predetermined level in a range of 0.0 to 20.0 MPaG which varies depending on the reaction type and conditions of the first fluid M.

Next, the other configuration of the reactor core 3 according to the present embodiment is described below.

As shown in FIG. 2 and FIG. 3, the second structure 9 located on the top side (the uppermost second structure 9) is provided with a lid structure (a lid member) 39 having a rectangular plate shape and covering the plural second flow channels 31. The second base plate 25 in the second structure 9 located on the bottom side (the lowermost second structure 9) is thicker than the other second plates 25 of the other second structures 9. The respective first structures 7 and the respective second structures 9 other than the second structure 9 located on the lowermost side have the same dimensions.

The end surfaces (the top surfaces) 13e of the first side walls 13, the end surfaces 15e of the first middle walls 15, and the end surface 19e of the first end wall 19 are joined to the lower surface 25u of the adjacent second base plate 25 (adjacent to the first structure 7) by diffusion bonding (an example of joining methods). The end surfaces (the top surfaces) 27e of the second side walls 27, the end surfaces 29e of the second middle walls 29, and the end surface 33e of the second end wall 33 are joined to the lower surface 11u of the adjacent first base plate 11 (adjacent to the second structure 9) or the lower surface 39u of the lid structure 39 by diffusion bonding. The reactor core 3, namely, the reactor 1 has a structure in which a predetermined number of the first structures 7 corresponding to the reactor capacity and the second structures 9 of which the number is equal to the predetermined number plus one are stacked alternately, and the lid structure 39 is placed on the uppermost second structure 9. The reactor 1 is manufactured such that the plural first structures 7, the plural second structures 9, and the lid structure 39 are joined together simultaneously by diffusion bonding under the arrangement conditions as described above.

The thickness T1 of the first side walls 13 is greater than the thickness T2 of the first middle walls 15, and the thickness S1 of the second side walls 27 is greater than the thickness S2 of the second middle walls 29. In particular, the ratio T1/T2 of the thickness T1 of the first side walls 13 to the thickness T2 of the first middle walls 15 is set at 4.0 or greater. The ratio S1/S2 of the thickness S1 of the second side walls 27 to the thickness S2 of the second middle walls 29 is set at 4.0 or greater. The reason the ratio T1/T2 and the ratio S1/S2 are each set at 4.0 or greater is that the joint area of the end surface 13e of the respective first side walls 13 and the joint area of the end surface 27e of the respective second side walls 27 are sufficiently ensured, so as to increase the structural strength (the strength to resist pressure) and the sealing performance to prevent leakage of the first fluid M and the like in the entire reactor core 3 (reactor 1). The thickness T3 of the first end wall 19 (see FIG. 4) is greater than or equal to the thickness T1 of the first side walls 13, and the thickness S3 of the second end wall 33 (see FIG. 5) is greater than or equal to the thickness S1 of the second side walls 27.

The ratio T5/T4 of the long-side length T5 to the short-side length T4 of the respective first flow channels 17 in cross section is set at 18.0 or less. The ratio S5/S4 of the long-side length S5 to the short-side length S4 of the respective second flow channels 31 in cross section is set at 18.0 or less. The reason the ratio T5/T4 and the ratio S5/S4 are each set at 18.0 or less is that the joint area of the end surface 15e of the respective first middle walls 15 and the joint area of the end surface 29e of the respective second middle walls 29 are sufficiently ensured, so as to increase the structural strength (the strength to resist pressure) and the sealing performance of the first flow channels 17 and the like. As used in the present embodiment, the short-side length T4 of the first flow channels 17 in cross section is the same as the depth of the first flow channels 17, and the short-side length S4 of the second flow channels 31 in cross section is the same as the depth of the second flow channels 31. The long-side length T5 of the first flow channels 17 is the same as the width of the first flow channels 17, and the long-side length S5 of the second flow channels 31 in cross section is the same as the width of the second flow channels 31.

The ratio T5/T2 of the width T5 of the first flow channels 17 to the thickness T2 of the first middle walls 15 is set at 1.0 or greater, preferably set at 2.0 to 4.0. The ratio S5/S2 of the width S5 of the second flow channels 31 to the thickness S2 of the second middle walls 29 is set at 1.0 or greater, preferably set at 2.0 to 4.0. The reason the ratio T5/T2 and the ratio S5/S2 are each set at 1.0 or greater is that the reaction space for the first fluid M is sufficiently provided in the first flow channels 17. The reason the ratio T5/T2 and the ratio S5/S2 are each preferably set at 2.0 or greater is that the reaction space for the first fluid M is more sufficiently provided in the first flow channels 17. The reason the ratio T5/T2 and the ratio S5/S2 are each preferably set at 4.0 or less is that the joint area of the end surface 15e of the respective first middle walls 15 and the joint area of the end surface 29e of the respective second middle walls 29 are sufficiently ensured, so as to increase the structural strength (the strength to resist pressure) and the sealing performance of the first flow channels 17 and the like. In the present embodiment, for example, the width T5 of the first flow channels 17 and the width S5 of the second flow channels 31 are each set at 2 to 60 mm.

The ratio T6/T2 of the thickness T6 of the first base plate 11 below the bottom of the respective first flow channels 17 (the thickness of the first base plate 11) to the thickness T2 of the respective first middle walls 15 is set at 0.2 to 5.0. The ratio S6/S2 of the thickness S6 of the second base plate 25 below the bottom of the respective second flow channels 31 (the thickness of the second base plate 25) to the thickness S2 of the respective second middle walls 29 is set at 0.2 to 5.0. The reason the ratio T6/T2 and the ratio S6/S2 are each set at 0.2 or greater is that the rigidity of the first base plate 11 and the rigidity of the second base plate 25 are sufficiently ensured, so as to increase the structural strength (the strength to resist pressure) and the sealing performance of the first flow channels 17 and the like. The reason the ratio T6/T2 and the ratio S6/S2 are each set at 5.0 or less is that the distance between the first flow channels 17 and the corresponding second flow channels 31 is decreased, so as to increase the efficiency of heat transfer between the first fluid M in the first flow channels 17 and the second fluid HC in the corresponding second flow channels 31.

The thickness S1 of the second side walls 27 is set to be the same as the thickness T1 of the first side walls 13, and the thickness S2 of the second middle walls 29 is set to be the same as the thickness T2 of the first middle walls 15. The thickness S3 of the second end wall 33 is set to be the same as the thickness T3 of the first end wall 19.

A catalyst member (catalyst structure) 41 placing a catalyst for accelerating the reaction of the first fluid M is removably provided in the respective first flow channels 17. The catalyst member 41 is made of stainless steel, for example, and extends in the lateral direction. The catalyst member 41 has a wave-like shape in cross section, for example. The catalyst is selected as appropriate depending on the type of the reaction of the first fluid M. When the reaction of the first fluid M is a steam reforming reaction of methane, the catalyst used is one or more kinds of metal selected from nickel (Ni), platinum (Pt), ruthenium (Ru), rhodium (Rh), palladium (Pd), cobalt (Co), rhenium (Re), and iridium (Ir). The catalyst may be applied on the respective first flow channels 17 (as an example of placing methods), instead of the catalyst member 41 removably provided in the respective first flow channels 17.

A pair of fins (baffles) 43 is removably provided in the respective second flow channels 31. The paired fins 43 are laid on top of each other in the vertical direction. The respective fins 43 are made of stainless steel, for example, and extend in the lateral direction. The fins 43 have a wave-like shape in cross section, for example.

Next, the peripheral configuration of the reactor core 3 according to the present embodiment is described below.

As shown in FIG. 1 and FIG. 4, a first introduction chamber (an example of hollow first introduction members) 45 having a dome-like shape for introducing the first fluid M into the respective first flow channels 17 is removably provided on the left side of the reactor core 3. The first introduction chamber 45 connects with the respective first flow channels 17. The first introduction chamber 45 is provided with a raw material supply port 47. The raw material supply port 47 is connected to a raw material supply source (not shown) for supplying the first fluid M.

A first exhaust chamber (an example of hollow first exhaust members) 49 having a box shape for collecting and exhausting the product P led out of the respective first leading-out ports 21 is provided on the right side on the front surface of the reactor core 3. The first exhaust chamber 49 extends in the vertical direction and connects with the respective first leading-out ports 21. A product exhaust port 51 is provided at the center portion, the end portion, the upper portion or the lower portion of the first exhaust chamber 49. The product exhaust port 51 is connected to another treatment device (not shown) for subjecting the product P to aftertreatment.

As shown in FIG. 1 and FIG. 5, a second introduction chamber (an example of hollow second introduction members) 53 having a dome-like shape for introducing the second fluid into the respective second flow channels 31 is removably provided on the right side of the reactor core 3. The second introduction chamber 53 connects with the respective second flow channels 31. The second introduction chamber 53 is provided with a heat medium supply port 55. The heat medium supply port 55 is connected to a heat medium supply source (not shown) for supplying the second fluid HC.

A second exhaust chamber (an example of hollow second exhaust members) 57 having a box shape for collecting and exhausting the second fluid HC led out of the respective second leading-out ports 35 is provided on the left side on the front surface of the reactor core 3. The second exhaust chamber 57 extends in the vertical direction and connects with the respective second leading-out ports 35. A heat medium exhaust port 59 is provided at the center portion, the end portion, the upper portion or the lower portion of the second exhaust chamber 57. The heat medium exhaust port 59 is connected to a heat medium reclaiming apparatus (not shown) for reclaiming the second fluid HC.

Next, the operations and effects of the present embodiment are described below.

The first fluid M is supplied from the raw material supply source to the first introduction chamber 45 (toward the reactor core 3) via the raw material supply port 47, so that the first fluid M is introduced to and flows through the respective first flow channels 17 in the right direction of the drawings. The second fluid HC is supplied from the heat medium supply source to the second introduction chamber 53 (toward the reactor core 3) via the heat medium supply port 55, so that the second fluid HC is introduced to and flows through the respective second flow channels 31 in the left direction of the drawings which is the opposite direction (in the counter flow direction) of the flow direction of the first fluid M in the respective first flow channels 17. The heat exchange is then carried out between the first fluid M in the first flow channels 17 and the second fluid HC in the corresponding second flow channels 31, so as to heat or cool the first fluid M. In association with the reaction acceleration due to the catalyst placed in the respective catalyst members 41, the first fluid M is reacted (subjected to an endothermic reaction or an exothermic reaction), so as to produce the product P. The produced product P is led into the first exhaust chamber 49 through the respective first leading-out ports 21 to be exhausted from the product exhaust port 51 toward the other treatment apparatus. The second fluid HC used for the heat exchange is led into the second exhaust chamber 57 through the respective second leading-out ports 35 to be exhausted from the heat medium exhaust port 59 toward the heat medium reclaiming apparatus.

Since the heat exchange is carried out between the first fluid M in the first flow channels 17 and the second fluid HC in the corresponding second flow channels 31, heat can be supplied substantially equally to the respective first flow channels 17 regardless of the number of the first structures 7 and the second structures 9 to be stacked.

Since the end surface 13e of the respective first side walls 13, the end surface 15e of the respective first middle walls 15, and the like are joined to the lower surface 25u of the respective adjacent second base plates 25 by diffusion bonding, the structural strength (the strength to resist pressure) and the sealing performance to prevent leakage of the first fluid M and the like in each of the first flow channels 17 can be obtained (ensured). In addition, the end surface 27e of the respective second side walls 27, the end surface 29e of the respective second middle walls 29, and the like are joined to the lower surface 11u of the respective adjacent first base plates 11 or the lower surface 39u of the lid structure 39 by diffusion bonding. Thus, the structural strength (the strength to resist pressure) and the sealing performance to prevent leakage of the second fluid HC in each of the second flow channels 31 can be obtained (ensured). Particularly, the ratio T5/T4 and the ratio S5/S4 are each set at 18.0 or less, so as to ensure the joint area of the end surface 15e of the respective first middle walls 15 and the like more sufficiently and further increase the structural strength (the strength to resist pressure) and the sealing performance of the respective first flow channels 17 and the like.

The thickness T1 of the first side walls 13 is greater than the thickness T2 of the first middle walls 15, and the thickness S1 of the second side walls 27 is greater than the thickness S2 of the second middle walls 29. Thus, the structural strength (the strength to resist pressure) and the sealing performance of the entire reactor core 3 (reactor 1) can be obtained (ensured) without the reactor core 3 housed in a container (pressure vessel) resistant to a pressure difference between the inside and the outside. Particularly, the ratio T1/T2 and the ratio S1/S2 are each set at 4.0 or greater, so as to ensure the joint area of the end surface 13e of the respective first side walls 13 and the like more sufficiently and further increase the structural strength (the strength to resist pressure) and the sealing performance of the reactor core 3.

The length of at least one side of the respective first flow channels 17 in cross section is set at several millimeters, and the specific surface area of the respective first flow channels 17 per unit of volume is large. The pair of the fins 43 can generate a turbulent flow of the second fluid HC in the respective second flow channels 31 and increase the heat transfer area inside the respective second flow channels 31. Accordingly, the efficiency of heat transfer between the first fluid M in the first flow channels 17 and the second fluid HC in the corresponding second flow channels 31 increases. Particularly, the ratio T6/T2 and the ratio S6/S2 are each set at 0.2 to 5.0, so as to further increase the efficiency of heat transfer between the first fluid M in the first flow channels 17 and the second fluid HC in the corresponding second flow channels 31, while ensuring the rigidity of the first base plates 11 and the like more sufficiently.

The first introduction chamber 45 is removably attached to the reactor core 3 on the left side, so as to facilitate the replacement of the catalyst members 41 from the left side of the reactor core 3 when the catalyst placed on the catalyst members 41 is deteriorated. In addition, the second introduction chamber 53 is removably attached to the reactor core 3 on the right side, so as to facilitate the replacement of the fins 43 from the right side of the reactor core 3 when the fins 43 are damaged.

According to the present embodiment, heat can be applied substantially equally to the respective first flow channels 17 regardless of the number of the first structures 7 and the like to be stacked, and the structural strength (the strength to resist pressure) of the reactor core 3 can be ensured sufficiently without the reactor core 3 housed in a container (pressure vessel). Thus, the reactor 1 can increase flexibility in changing the reactor capacity such that the number of the first structures 17 and the like to be stacked is merely changed without great change in design of the entire reactor 1. Accordingly, the possibility of design of the reactor 1 can be expanded while dealing with the change in the capacity of the reactor 1.

The structural strength (the strength to resist pressure) of the reactor core 3 can be ensured sufficiently without the reactor core 3 housed in a container. Accordingly, the configuration of the reactor 1 can be simplified while a container is eliminated from the elements of the reactor 1, so as to prevent an increase in size of the reactor 1 to contribute to a reduction in space for the reactor 1.

In addition to the effects according to the present embodiment described above, since the efficiency of heat transfer between the first fluid M in the first flow channels 17 and the second fluid HC in the corresponding second flow channels 31 increases, the reaction speed of the first fluid M and the yield of the product P can be improved. Further, the reactor 1 facilitates the replacement of the catalyst members 41 from the left side of the reactor core 3 when the catalyst placed on the catalyst members 41 is deteriorated, and facilitates the replacement of the fins 43 from the right side of the reactor core 3 when the fins 43 are damaged. Accordingly, the performance of maintenance of the reactor 1 can be improved.

In the present embodiment, the configuration of the reactor core 3 may be modified as follows.

An alternative to the case in which the first end wall 19 is provided on the right side on one surface of the first base plate 11, the first leading-out port 21 is provided on the right side on one of or both of the first side walls 13, and the first connection flow channel 23 is provided on the right side on one surface of the first base plate 11, is described below. For example, the respective first flow channels 17 may be open on the right side so as to lead the product P. In such a case, another second end wall (not shown) for preventing the product P from flowing into the respective second flow channels 31 is provided on the right side on one surface of the second base plate 25, and a second introduction port (not shown) for introducing the second fluid HC therefrom is provided on the right side on one of or both of the second side walls 27. The second base plate 25 is provided with another second connection flow channel (not shown) by which the second introduction port connects with the second flow channels 31 on the right side and which is provided on the right side on one surface of the second base plate 25. Instead of the first exhaust chamber 49 having a box shape provided on the right side on the front surface of the reactor core 3, a first exhaust chamber (not shown) having a dome-like shape is provided on the right side of the reactor core 3. Instead of the second introduction chamber 53 having a dome-like shape provided on the right side of the reactor core 3, a second introduction chamber (not shown) having a box shape is provided on the right side on the front surface of the reactor core 3.

Modified Example 1

Modified example 1 of the present embodiment is described below with reference to FIG. 6 and FIG. 7.

While FIG. 4 illustrates the case in which the respective first flow channels 17 are open on the left side, FIG. 6 illustrates the case in which the respective first flow channels 17 are open on the right side so as to lead the product P out of the first base plate 11. The first end wall 19 is provided not on the right side but on the left side on one surface of the first base plate 11. While FIG. 4 illustrates the case in which the first leading-out port 21 is provided on the right side on one of or both of the first side walls 13, FIG. 6 illustrates the case in which a first introduction port 61 for introducing the first fluid M therefrom is provided on the left side on one of or both of the first side walls 13. While FIG. 4 illustrates the case in which the first connection flow channel 23 is provided on the right side on one surface of the first base plate 11, FIG. 6 illustrates the case in which a first connection flow channel 63 by which the first introduction port 61 connects with the first flow channels 17 on the left side is provided on the left side on one surface of the first base plate 11. The first connection flow channel 63 extends in the front-rear direction.

Figure 7:
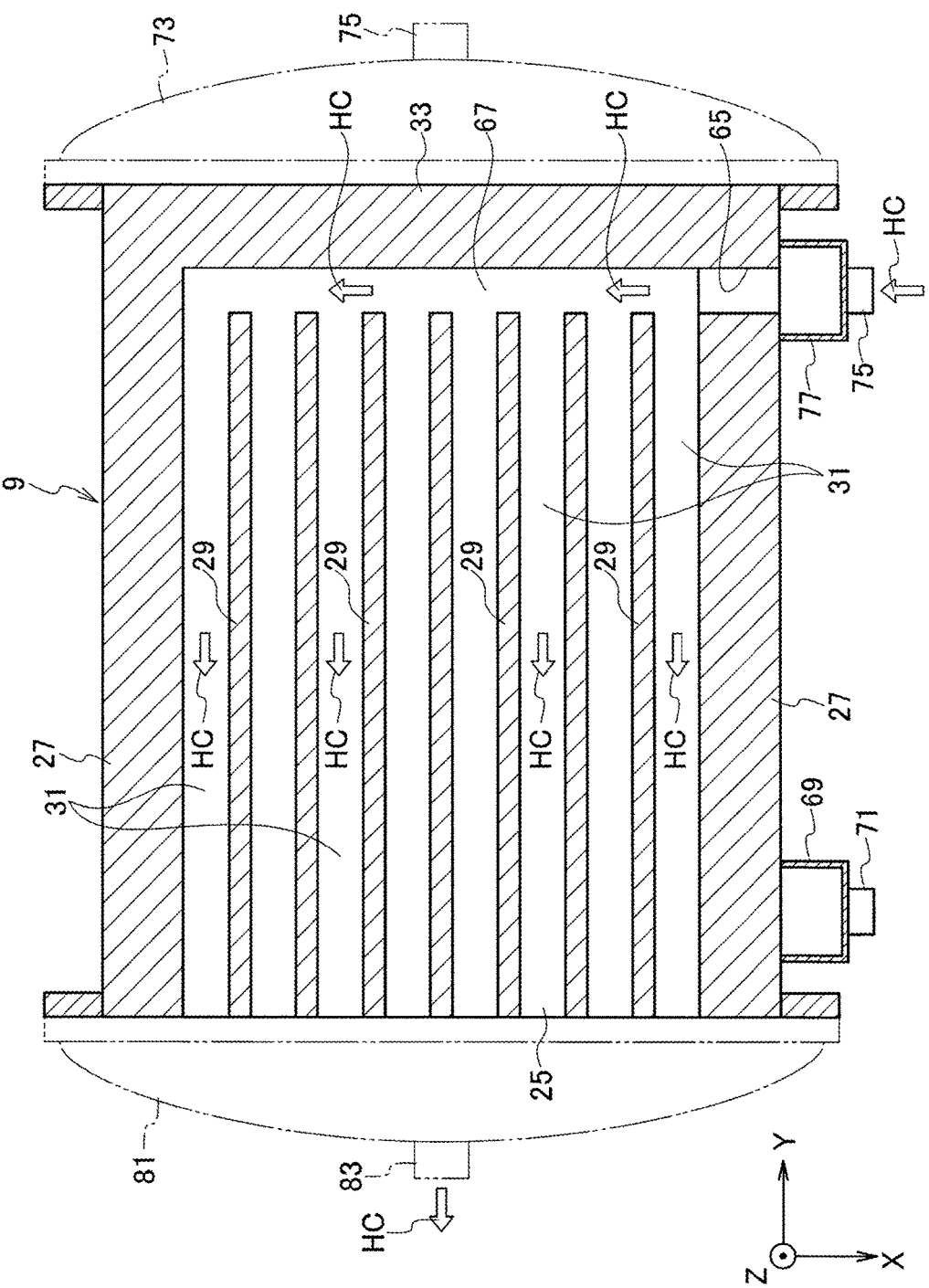
FIG. 7 is a cross-sectional view for illustrating modified example 1 of one embodiment.

While FIG. 5 illustrates the case in which the respective second flow channels 31 are open on the right side, FIG. 7 illustrates the case in which the respective second flow channels 31 are open on the left side so as to lead the second fluid HC out of the second base plate 25. The second end wall 33 is provided not on the left side but on the right side on one surface of the second base plate 25. While FIG. 5 illustrates the case in which the second leading-out port 35 is provided on the left side on one of or both of the second side walls 27, FIG. 7 illustrates the case in which a second introduction port 65 for introducing the second fluid HC therefrom is provided on the right side on one of or both of the second side walls 27. Instead of the second connection flow channel 37 provided on the left side on one surface of the second base plate 25 (refer to FIG. 5), a second connection flow channel 67 by which the second introduction port 65 connects with the second flow channels 31 on the right side is provided on the right side on one surface of the second base plate 25. The second connection flow channel 67 extends in the front-rear direction.

While FIG. 4 illustrates the case in which the first introduction chamber 45 having a dome-like shape is removably provided on the left side of the reactor core 3, FIG. 6 illustrates the case in which a first introduction chamber (an example of hollow first introduction members) 69 having a box shape for introducing the first fluid M into the first flow channels 17 through the respective first introduction ports 61 is provided on the left side of the reactor core 3. The first introduction chamber 69 extends in the vertical direction and connects with the respective first introduction ports 61. A raw material supply port 71 connected to the raw material supply source is provided at the center portion, the end portion, the upper portion or the lower portion of the first introduction chamber 69.

While FIG. 4 illustrates the case in which the first exhaust chamber 49 having a box shape is provided on the right side on the front surface of the reactor core 3, FIG. 6 illustrates the case in which a first exhaust chamber (an example of hollow first exhaust members) 73 having a dome-like shape for collecting and exhausting the product P led out of the respective first flow channels 17 is provided on the right side of the reactor core 3. The first exhaust chamber 73 connects with the respective first flow channels 17. The first exhaust chamber 73 is provided with a product exhaust port 75 connected to the other treatment device.

While FIG. 5 illustrates the case in which the second introduction chamber 53 is provided on the right side of the reactor core 3, FIG. 7 illustrates the case in which a second introduction chamber (an example of hollow second introduction members) 77 having a box shape for introducing the second fluid HC into the second flow channels 31 through the respective second introduction ports 65 is provided on the right side of the reactor core 3. The second introduction chamber 77 extends in the vertical direction and connects with the respective second introduction ports 65. A heating medium supply port 75 connected to the heat medium supply source is provided at the center portion, the end portion, the upper portion or the lower portion of the second introduction chamber 77.

While FIG. 5 illustrates the case in which the second exhaust chamber 57 is provided on the left side on the front surface of the reactor core 3, FIG. 7 illustrates the case in which a second exhaust chamber (an example of hollow second exhaust members) 81 having a dome-like shape for collecting and exhausting the second fluid HC led out of the respective second flow channels 31 is provided on the left side of the reactor core 3. The second exhaust chamber 81 connects with the respective second flow channels 31, and the second exhaust chamber 81 is provided with a heat medium exhaust port 83 connected to the heat medium reclaiming apparatus.

The effects of modified example 1 different from the effects of the present embodiment are described below.

The first fluid M is supplied from the raw material supply source to the first introduction chamber 69 via the raw material supply port 71, and then introduced into the respective first flow channels 17 through the respective first introduction ports 61 and further flows through the respective first flow channels 17 in the right direction of the drawings (from the inlet side to the outlet side). The second fluid HC is supplied from the heat medium supply source to the second introduction chamber 77 via the heat medium supply port 75, and then introduced into the respective second flow channels 31 through the respective second introduction ports 65 and further flows through the respective second flow channels 31 in the left direction of the drawings (from the inlet side to the outlet side). The heat exchange is then carried out between the second fluid HC in the second flow channels 31 and the first fluid M in the corresponding first flow channels 17, namely, between the first fluid M and the second fluid HC flowing counter to each other, so as to heat or cool the first fluid M. In association with the reaction acceleration due to the catalyst placed in the respective catalyst members 41, the first fluid M is reacted (subjected to an endothermic reaction or an exothermic reaction), so as to produce the product P. The produced product P is led into the first exhaust chamber 73 from the outlet side of the respective first flow channels 17 and exhausted from the product exhaust port 75 toward the other treatment apparatus. The second fluid HC used for the heat exchange is led into the second exhaust chamber 81 from the outlet side of the respective second flow channels 31 and exhausted from the heating medium exhaust port 83 toward the heat medium reclaiming apparatus.

The first introduction chamber 73 is removably attached to the reactor core 3 on the right side, so as to facilitate the replacement of the catalyst members 41 from the right side of the reactor core 3 when the catalyst placed on the catalyst members 41 is deteriorated. In addition, the second introduction chamber 81 is removably attached to the reactor core 3 on the left side, so as to facilitate the replacement of the fins 43 from the left side of the reactor core 3 when the fins 43 are damaged.

Modified example 1 can also achieve the same effects as the present embodiment described above.

In modified example 1, the configuration of the reactor core 3 may be modified as follows.

In the embodiment described above, the second end wall 33 is provided on the right side on one surface of the second base plate 25, and the second introduction port 65 is provided on the right side on one of or both of the second side walls 27. The second connection flow channel 67 is formed on the right side on one surface of the second base plate 25. Instead, in modified example 1, the respective second flow channels 31 are open on the right side so as to introduce the second fluid HC therefrom. In this case, another first end wall (not shown) for preventing the second fluid HC from flowing into the respective first flow channels 17 is provided on the right side on one surface of the first base plate 11, and a first leading-out port (not shown) for leading the product P out of the first base plate 11 is provided on the right side on one of or both of the first side walls 13. The first base plate 11 is provided with another first connection flow channel (not shown) by which the first leading-out port connects with the plural first flow channels 17 on the right side and which is provided on the right side on one surface of the first base plate 11. Instead of the first exhaust chamber 73 having a dome-like shape provided on the right side on the front surface of the reactor core 3, a first exhaust chamber (not shown) having a box shape is provided on the right side on the front surface of the reactor core 3. Instead of the second introduction chamber 77 having a box shape provided on the right side on the front surface of the reactor core 3, a second introduction chamber (not shown) having a dome-like shape is provided on the right side of the reactor core 3.

Modified Example 2

Modified example 2 of the present embodiment is described below with reference to FIG. 8A.

As shown in FIG. 8A, in addition to the first side walls 13 and the plural first middle walls 15 provided on one surface (the upper surface) of the first base plate 11, auxiliary first side walls 85 are provided on the front and rear sides on the other surface (the lower surface) of the first base plate 11. A plurality of auxiliary first middle walls 87 are arranged at regular intervals in the front-rear direction (in the X direction) between the pair of the auxiliary first side walls 85 on the other surface of the first base plate 11. The respective auxiliary first side walls 85 project downward (in the other direction: the minus direction of the Z direction) and extend in the lateral direction (in the Y direction), and the end surfaces (the top surfaces) 85e of the auxiliary first side walls 85 are joined to the end surfaces 27e of the corresponding second side walls 27 by diffusion bonding (an example of joining methods). The respective auxiliary first middle walls 87 project downward and extend in the lateral direction, and the end surfaces 87e of the auxiliary first middle walls 87 are joined to the end surfaces 29e of the corresponding second middle walls 29 by diffusion bonding.

In addition to the second side walls 27 and the plural second middle walls 29 provided on one surface of the second base plate 25, auxiliary second side walls 89 are provided on the front and rear sides on the other surface of the second base plate 25. A plurality of auxiliary second middle walls 91 are arranged at regular intervals in the front-rear direction between the pair of the auxiliary second side walls 89 on the other surface of the second base plate 25. The respective auxiliary second side walls 89 project downward and extend in the lateral direction, and the end surfaces 89e of the auxiliary second side walls 89 are joined to the end surfaces 13e of the corresponding first side walls 13 by diffusion bonding. The respective auxiliary second middle walls 91 project downward and extend in the lateral direction, and the end surfaces 91e of the auxiliary second middle walls 91 are joined to the end surfaces 15e of the corresponding first middle walls 15 by diffusion bonding.

Modified example 2 can also achieve the same operations and effects as the present embodiment described above.

Modified Example 3

Modified example 3 of the present embodiment is described below with reference to FIG. 8B.

As shown in FIG. 8B, in addition to the first side walls 13 and the plural first middle walls 15 provided on one surface (the upper surface) of the first base plate 11, a plurality of auxiliary reaction walls 93 are arranged at intervals in the front-rear direction (in the X direction) on the other surface (the lower surface) of the first base plate 11. The auxiliary reaction walls 93 project downward (in the other direction: the minus direction of the Z direction) and extend in the lateral direction (in the Y direction), and the end surfaces (the tips) 93e of the auxiliary reaction walls 93 are joined to one surface of the second base plate 25 (the bottom surfaces of the second flow channels 31) by diffusion bonding.

In addition to the second side walls 27 and the plural second middle walls 29 provided on one surface of the second base plate 25, a plurality of auxiliary temperature control walls 95 are arranged at intervals in the front-rear direction on the other surface of the second base plate 25. The auxiliary temperature control walls 95 project downward and extend in the lateral direction, and the end surfaces 95e of the auxiliary temperature control walls 95 are joined to one surface of the first base plate 11 (the bottom surfaces of the first flow channels 17) by diffusion bonding.

Modified example 3 can also achieve the same operations and effects as the present embodiment described above.

The present disclosure is not intended to be limited to the description of the embodiments described above, and may be applicable to various modes, such as a case in which at least a pair of either the first structures 7 or the second structures 9 laid on top of each other is stacked on the other one of the first structures 7 and the second structures 9.

For example, the first fluid M subjected to an endothermic reaction to produce a product is supplied to the first flow channels 17, and the second fluid HC subjected to an exothermic reaction to produce a product is supplied to the second flow channels 31. In such a case, as the second fluid HC flows through the second flow channels 31, the exothermic reaction is caused to generate heat of reaction. The heat of reaction thus generated can be used for a heat source for the endothermic reaction to be caused in the first flow channels 17. Accordingly, the heat can be used effectively.

It should be noted that the present disclosure includes various embodiments which are not disclosed herein. Therefore, the scope of the present disclosure is defined only by the matters specified according to the claims reasonably derived from the description described above.

What is claimed is:

1. A reactor for causing a reaction of a first fluid by a heat exchange between the first fluid and a second fluid to generate a product, the reactor comprising:

a plurality of first structures each including: first side walls provided on both sides in a first direction on one surface of a first base plate and extending in a second direction perpendicular to the first direction; a plurality of first middle walls arranged at intervals in the first direction between the paired first side walls on the one surface of the first base plate and extending in the second direction; and first flow channels provided between each first side wall and the adjacent first middle wall and between the respective first middle walls adjacent to each other so that the first fluid flows therethrough;

a plurality of second structures coexisting with and stacked on the plural first structures in a third direction perpendicular to the first direction and the second direction, the second structures each including: second side walls provided on both sides in the first direction on one surface of a second base plate and extending in the second direction; a plurality of second middle walls arranged at intervals in the first direction between the paired second side walls on the one surface of the second base plate and extending in the second direction; and second flow channels provided between each second side wall and the adjacent second middle wall and between the respective second middle walls adjacent to each other so that the second fluid flows therethrough; and a lid structure provided on the second structure located on one end side in the third direction to cover the plural second flow channels, wherein end surfaces of the first side walls and end surfaces of the first middle walls are joined to the adjacent second structure, end surfaces of the second side walls and end surfaces of the second middle walls are joined to the adjacent first structure or the lid structure, a thickness of the first side walls is greater than or equal to a thickness of the first middle walls, and a thickness of the second side walls is greater than or equal to a thickness of the second middle walls.

2. The reactor according to claim 1, wherein a predetermined number of the first structures corresponding to a reactor capacity coexist with and are stacked on the plural second structures, and the first structures, the second structures, and the lid structure are joined together simultaneously in a state in which the lid structure is provided on the second structure located on the one end side in the third direction.

3. The reactor according to claim 1, wherein the plural first structures and the plural second structures are alternately stacked in the third direction.

4. The reactor according to claim 1, wherein a ratio of the thickness of the first side walls to the thickness of the first middle walls and a ratio of the thickness of the second side walls to the thickness of the second middle walls are each set at 4.0 or greater.

5. The reactor according to claim 1, wherein the first flow channels and the second flow channels each have a rectangular shape in cross section, and a ratio of a long-side length to a short-side length of the first flow channels in cross section and a ratio of a long-side length to a short-side length of the second flow channels in cross section are each set at 18.0 or less.

6. The reactor according to claim 1, wherein a ratio of a width of the first flow channels to the thickness of the first middle walls and a ratio of a width of the second flow channels to the thickness of the second middle walls are each set at 1.0 or greater.

7. The reactor according to claim 1, wherein a ratio of a thickness of the first base plate below a bottom of the respective first flow channels to the thickness of the first middle walls and a ratio of a thickness of the second base plate below a bottom of the respective second flow channels to the thickness of the second middle walls are each set at 0.2 to 5.0.

8. The reactor according to claim 1, wherein the thickness of the second side walls is set to be the same as the thickness of the first side walls, and the thickness of the second middle walls is set to be the same as the thickness of the first middle walls.

9. The reactor according to claim 1, wherein a catalyst for accelerating the reaction of the first fluid is placed in the respective first flow channels.

10. The reactor according to claim 9, wherein a catalyst member placing the catalyst is removably provided in the respective first flow channels.

11. The reactor according to claim 1, wherein a fin is removably provided in the respective second flow channels.

12. The reactor according to claim 1, wherein:

a first end wall for preventing the second fluid from flowing into the respective first flow channels is provided on an one side in the second direction on the one surface of the respective first base plates, a first leading-out port for leading the product out of the first flow channels is provided on the one side in the second direction on at least one of the first side walls in the respective first structures, and a first connection flow channel by which the first leading-out port connects with the respective first flow channels on the one side in the second direction is provided on the first side in the second direction on one surface of the respective first structures;

a second end wall for preventing the first fluid from flowing into the respective second flow channels is provided on another side in the second direction on the one surface of the respective second base plates, a second leading-out port for leading the second fluid out of the second flow channels is provided on the other side in the second direction on at least one of the second side walls in the respective second structures, and a second connection flow channel by which the second leading-out port connects with the respective second flow channels on the other side in the second direction is provided on the second side in the second direction on one surface of the respective second structures;

an end surface of the first end wall is joined to the adjacent second structure or the adjacent first structure; and an end surface of the second end wall is joined to the adjacent first structure, the adjacent second structure, or the lid structure.

13. The reactor according to claim 12, further comprising:

a hollow first introduction member removably attached to a reactor core on the other side in the second direction so as to introduce the first fluid into the respective first flow channels, the reactor core having a configuration in which the plural first structures coexist with and are stacked on the plural second structures;

a hollow first exhaust member attached to the reactor core so as to collect and exhaust the product led out of the respective first leading-out ports;

a hollow second introduction member removably attached to the reactor core on the one side in the second direction so as to introduce the second fluid into the respective second flow channels; and a hollow second exhaust member attached to the reactor core so as to collect and exhaust the second fluid led out of the respective second leading-out ports.

14. The reactor according to claim 12, wherein a joining method regarding the end surfaces of the first side walls, the end surfaces of the first middle walls, and the end surface of the first end wall in each first plate is diffusion bonding, and a joining method regarding the end surfaces of the second side walls, the end surfaces of the second middle walls, and the end surface of the second end wall in each second base plate is diffusion bonding.

15. The reactor according to claim 1, wherein:

a first end wall for preventing the second fluid from flowing into the respective first flow channels is provided on an one side in the second direction on the one surface of the respective first base plates, a first introduction port for introducing the first fluid is provided on the one side in the second direction on at least one of the first side walls in the respective first structures, and a first connection flow channel by which the first introduction port connects with the respective first flow channels on the one side in the second direction is provided on the second side in the second direction on one surface of the respective first structures;

a second end wall for preventing the first fluid from flowing into the respective second flow channels is provided on another side in the second direction on the one surface of the respective second base plates, a second introduction port for introducing the second fluid is provided on the other side in the second direction on at least one of the second side walls in the respective second structures, and a second connection flow channel by which the second introduction port connects with the respective second flow channels on the other side in the second direction is provided on the first side in the second direction on one surface of the respective second structures;

an end surface of the first end wall is joined to the adjacent second structure or the adjacent first structure; and an end surface of the second end wall is joined to the adjacent first structure, the adjacent second structure, or the lid structure.

16. The reactor according to claim 15, further comprising:

a hollow first introduction member attached to a reactor core so as to introduce the first fluid into the respective first flow channels from the respective first introduction ports, the reactor core having a configuration in which the plural first structures coexist with and are stacked on the plural second structures;

a hollow first exhaust member removably attached to the reactor core on the one side in the second direction so as to collect and exhaust the product led out of the respective first flow channels;

a hollow second introduction member attached to the reactor core so as to introduce the second fluid into the respective second flow channels from the respective second introduction ports; and a hollow second exhaust member removably attached to the reactor core on the other side in the second direction so as to collect and exhaust the second fluid led out of the respective second structures.

17. The reactor according to claim 15, wherein a joining method regarding the end surfaces of the first side walls, the end surfaces of the first middle walls, and the end surface of the first end wall in each first plate is diffusion bonding, and a connection method regarding the end surfaces of the second side walls, the end surfaces of the second middle walls, and the end surface of the second end wall in each second base plate is diffusion bonding.

18. The reactor according to claim 1, wherein a maximum pressure in the respective first flow channels and the respective second flow channels when the reactor is in operation is set at 0.0 to 20.0 MPaG.

* * * * *